United States Patent [19]

Robertson et al.

[11] Patent Number: 5,290,677

[45] Date of Patent: Mar. 1, 1994

[54] RAPID AND SENSITIVE TEST FOR DETECTING HEPATITIS A VIRUS

[75] Inventors: Betty H. Robertson, Chamblee; Omana V. Nainan, Decatur; Vicki K. Brown, Dunwoody; Harold S. Margolis, Lilburn; Bhawna Khanna, Lawrenceville, all of Ga.

[73] Assignee: The United States of America as represented by the Department of Health and Human Services, Washington, D.C.

[21] Appl. No.: 828,444

[22] Filed: Jan. 31, 1992

Related U.S. Application Data

[63] Continuation-in-part of Ser. No. 469,143, Jan. 24, 1990, abandoned.

[51] Int. Cl.[5] .................... C12Q 1/70; C12P 19/34; C07H 21/04
[52] U.S. Cl. .................... 435/5; 536/24.32; 536/24.33
[58] Field of Search ............ 435/91, 5; 536/27, 24.3, 536/24.32, 24.33; 935/78

[56] References Cited

U.S. PATENT DOCUMENTS 5,075,212 12/1991 Rotbart .................... 435/5

OTHER PUBLICATIONS

Cohen et al. (1987) Complete Nucleotide Sequence of Wild-Type Hepatitis A Virus: Comparison with Different Strains of Hepatitis A Virus and Other Picornaviruses, *J. of Virology* 61(1), 50–59.
Jansen et al. (1985) Combined Immunoaffinity cDNA–RNA Hybridization Assay for Detection of Hepatitis A Virus in Clinical Specimens *J. Clinical Microbiology* 22(6), 984–989.
Brown & Robertson (1990) Immunoselection of Clinical Specimens Containing Virus Followed by Polymersase Chain Reactor Amplification and Rapid Direct Sequencing *Biotechniques* 8(3), 262–264.
Robertson et al. (1991) Epidemiologic Patterns of Wild-Type Hepatitis A Virus Determined by Genetic Variation *J. Infectious Diseases* 163, 286–292.
Hayashi et al. (1989) Use of Labeled Primers in Polymerase Chain Reaction (LP–PCR) for a Rapid Detection of the Product *Nucleic Acids Res.* 17, 3605.
Brown et al., (1989) Characterization of a Simian Hepatitis A Virus (HAV): Antigenic & Genetic Comparison with Human HAV *J. Virology* 63(11), 4932–7.

Primary Examiner—Margaret Parr
Assistant Examiner—Kenneth R. Horlick
Attorney, Agent, or Firm—Needle & Rosenberg

[57] ABSTRACT

Provided are methods for detecting hepatitis A virus (HAV) and HAV genotypes I and III by capturing whole hepatitis A virus with antibodies specific to hepatitis A virus, generating a cDNA copy of the RNA by reverse transcription in the presence of a negative strand primer having the sequence defined by SEQ ID NO:1, amplifying the cDNA by polymerase chain reaction with both the negative strand primer and a labelled or unlabelled positive strand primer having the sequence defined by SEQ ID NO: 2, and detecting the amplified cDNA by hybridization with either or both of the probes defined by SEQ ID NO:3 and SEQ ID NO:4 or by detection of label, wherein the presence of detectable hybridization or amplification indicates the presence of hepatitis A virus. Also provided are DNA primers and probes from the amino-terminal portion of the VPI region of the HAV genome that selectively hybridize with HAV, HAV genotype I and HAV genotype III and can amplify the amino-terminal portion of the VPI region of HAV.

7 Claims, 5 Drawing Sheets

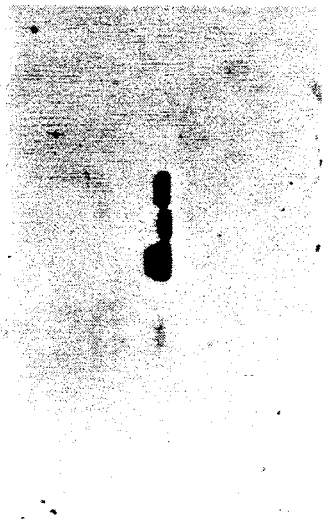
FIG. 2B
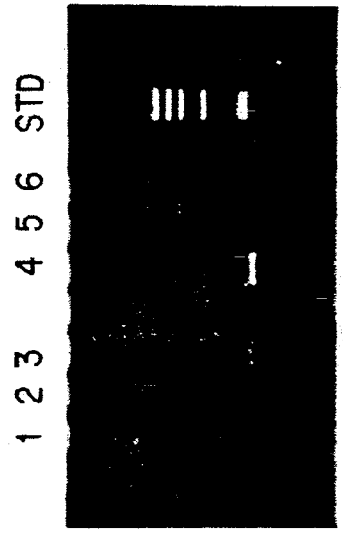
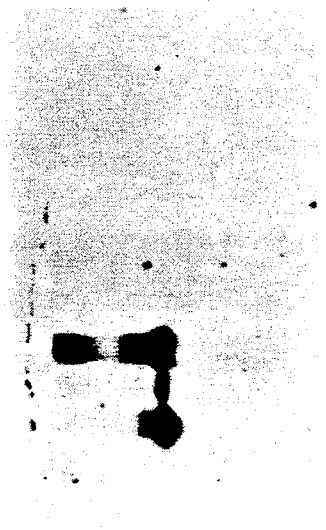
FIG. 2A
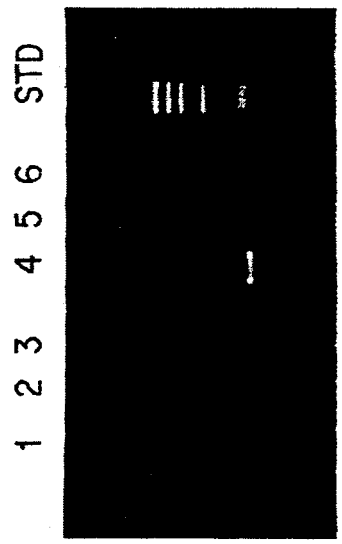

```
          2208                                                                              2257
Consensus GTTGGAGATG ATTCTGGAGG CTTCTCTACC ACTGTTTCAA CAAAACAGAA
    Ga76  ---------- ---------- ---------- ---------- ----------
    Pa21  -------G-- ---------- ---------- ---------- ----------
  India90 ---------- ---------- ---------- ---------- ----------
  Nepal89 ---------- ---------- --T------- --C------- ----------
  Nepal90 ---------- ---------- ---------- ---------- ----------
   HM175  ---------- ---------- -T-T-A--A- --A------- --T-----G-

2258                                                                              2307
Consensus TGTTCCAGAC CCCCAAGTTG GTATCACAAC AGTGAAGGAT CTTAAAGGTA
    Ga76  ---------- ---------- ---------- ---------- ----------
    Pa21  ---------- ---T------ ---C--T--- ---T------ ----------
  India90 ---------- ---------- -----T---- ---------- ----------
  Nepal89 ---------- ---T------ ---------- --------A- ----------
  Nepal90 ---------- ---------- ---C------ ---------- ----------
   HM175  ---------- ---------T ------A--- ---CA---A- T-G-----A-

2308                                                                              2357
Consensus GAGCAAACCA AGGGAAAATG GATATTTCGG GTGTCCAAGC TCCTGTGGGA
    Ga76  ---------- ---------- ---------- ---------- ----------
    Pa21  ---T------ ---------- ----G----- ---A------ ------A---
  India90 ---------- ---------- ---------- ---------- ----------
  Nepal89 -----G---- ---------- ---------- ---------- ------A---
  Nepal90 ---------- ---------- ---------- ---A------ ----------
   HM175  A---T---AG ---------- ----G----A ---A-A---- ---------A 2358
Consensus GCTATTACTA CCATTGAAGA T
    Ga76  ---------- ---------- -
    Pa21  --------C- -----G---- -
  India90 ---------- ---------- -
  Nepal89 -----G---- ---------- -
  Nepal90 ---------- ---------- -
   HM175  -------C-- -A--A----G -
```

FIG.3

Sequence of Probes Used to Differentiate VP1 Amino Terminus
of Genotype I and III (A) + 2232 Genotype I Probe (Nucleotides 2232 - 2251)

5'TCAACAACAG TTTCTACAGA 3'

(B) - 2328 Genotype III Probe (Nucleotides 2328 - 2301)

5'CCATTTTCCCTTGGTTTGCTC 3'

FIG.5

RAPID AND SENSITIVE TEST FOR DETECTING HEPATITIS A VIRUS

BACKGROUND OF THE INVENTION

This application is a continuation in part of U.S. application serial number 07/469,143, filed Jan. 24, 1990, abandoned, the entire contents of which are incorporated herein by reference.

The present invention relates, in general, to a method of detecting viral infection, and in particular, to methods of detecting hepatitis A virus infection. The invention also relates to methods for the differential detection of hepatitis A virus Genotype I and hepatitis A virus Genotype II.

Hepatitis A Virus (HAV), a hepatotropic Picornavirus, is the etiological agent of epidemic and endemic hepatitis A disease in many parts of the world. Morphologically, HAV is an icosahedral capsid, 27nm in diameter, composed of three exposed polypeptides, VP1, VP2, and VP3. The HAV genome is a single positive strand of RNA with a protein, VPg, which is covalently attached to the 5' end of the RNA. (Melnick, Intervirology 18:105 (1982); Gust et al., Intervirology 20:1(1983)).

Human isolates of hepatitis A virus (HAV) are a single serotype. A comparison of nucleotide sequences of HAV genomes confirms that the isolates studied have less than 10% sequence divergence (Robertson et al., Variation within hepatitis A VP1 amino acid and nucleotide sequences. in "Viral Hepatitis and Liver Disease". New York: Alan R. Liss pp.48-54 (1988)). However, recent data from limited genomic sequencing of larger panels of HAV isolates suggests that there are at least three genotypes within the serotype (Jansen et al., PNAS USA 87:2867 (1990); Robertson et al. J. Infectious Dis., 163:286 (1991)). Genotypes are characterized by nucleotide sequence differences of greater than 15-20% in selected regions of the capsid proteins. It has been proposed that these genetic groups be termed genotypes, I-III (Jansen et al., Molecular epidemiology of human hepatitis A virus (HAV), in "Viral Hepatitis and Liver Disease". Waldorf MD: Harper Graphics, Inc. (1991)). According to their terminology, group I comprises the bulk of human HAV isolates from around the world; group II has intermediate sequence diversity from genotype I and is represented by a single isolate CF-53 (France 1979; Jansen et al., PNAS USA 87:2867 (1990)); group III has >20% sequence diversity from geotype I and is comprised of a simian isolate from Panama (pA21, 1980; Lemon et al., Infection and Immunity 42:418 (1982)), a 1979 human isolate from Sweden (H-122; Jansen et al., PNAS USA 87:2867 (1990)) and a 1976 human isolate from Georgia, USA (GA76; Robertson et al., J. Infectious Dis. 163:286 (1991)).

Genotype I has been provisionally designated as the more prevalent human genetic variant. The group which includes the PA21-like genomes such as PA21, GA76, H-122, India 90, Nepal 89, and Nepal 90 isolates, has been proposed as genotype III (Jansen et al., Molecular epidemiology of human hepatitis A virus (HAV), in "Viral Hepatitis and Liver Disease". Waldorf MD: Harper Graphics, Inc. (1991)). The type II genotype in this nomenclature is composed of a single isolate which differs from Type I and Type III genotypes by about 15%.

Despite the extensive nucleic acid variability between genotypes I and III, there are limited amino acid changes within the external capsid polypeptides. The majority of the differences involve homologous amino acids with only 5 of the 20 genotype specific changes (VP2-40, I to P; VP3-39, P to A; VP3-145, G to H; VP1-37, R to Q; and VP1-277, S to D) resulting in an amino acid which might alter the structure of the capsid. The Type III genotype virus does not contain changed amino acids at position VP3-70 and VP1-102 found to be common to neutralization escape mutants (Ping et al., pNAS USA 85:8281 (1988)) and cynomolgus monkey HAV (Nainan et al., J. Gen. Virology (1991)). As there is no detectable difference in the expression of illness or the serological response to infection between genotype I and III, the conservation of these amino acids (VP3-70 and VP1-102) may be associated with the ability of these agents to cause illness in humans and produce cross protective antibodies.

The finding that HAV genotype III isolates were recovered from patients in northern India and the Kathmandu Valley of Nepal, raises the question what role this genotype places within India and Nepal. Most HAV isolates characterized thus far were from patients infected in the developed world, where rates of HAV infection are low. Analysis of additional isolates from the Indian subcontinent will be necessary to evaluate the proportion of HAV attributable to genotype III. Because the validity of a classification scheme is a function of its ability to reduce variance within groupings, we compared the nucleotide sequence of the exposed capsid polypeptides from HAV PA21 and HAV GA76, 2 of the 3 most divergent isolates identified to date. Despite their recovery from different species (Aotus monkey and humans), we hypothesized that they would have a high degree of homology, strengthening the genotype concept.

More than 90% of all HAV isolates examined have high sequence homology and belong to genotype I. We examined additional HAV isolates for evidence that genotype II or III cause endemic human disease (the identified genotype II and III human isolates came from France, Sweden and the USA where hepatitis A is relatively sporadic). Nucleic acid sequencing of the amino terminal region of the VP1 genome has provided evidence for genotype III viruses within Nepal and India. This genotype of HAV appears to be circulating in some parts of the world where HAV is hyperendemic, and is a potential cause of HAV infection within a susceptible population. It is clear, then, that a need exists for rapid and reliable methods of detecting infection by HAV, genotypes I and III.

SUMMARY OF THE INVENTION

The present invention relates generally to methods of rapidly determining the genotype of HAV based upon the use of primers which have been found to readily amplify all isolates examined thus far, and more particularly to methods of selectively delineating two of the human genotypes, which appear to be the more common HAV isolates responsible for illness in different parts of the world.

Accordingly, it is an object of the present invention to provide a method for detecting genotypes I or III of HAV comprising the steps of (i) isolating RNA from HAV, (ii) denaturing the RNA in the presence of a negative sense primer which recognizes all known genotypes of HAV, and after effecting hybridization of the primer and the RNA, generating a cDNA copy of the RNA by reverse transcription, (iii) adding a second positive sense primer which also binds to all known genotypes of HAV and is labeled at the 5' end, and annealing that second primer to the cDNA of step (ii), (iv) amplifying the annealed cDNA of step (iii) by polymerase chain reaction, and (v) detecting the amplified cDNA of step (iv).

It is a further object of the present invention to provide a method for detecting genotypes I or III of HAV comprising the steps of (i) isolating HAV RNA, (ii) denaturing the RNA in the presence of the primers which recognize all known genotypes of HAV, and after annealing with that primer, generating a cDNA copy of the RNA by reverse transcription, (iii) amplifying the annealed cDNA of step (ii) by polymerase chain reaction, and (iv) detecting the amplified cDNA of step (iii) as HAV DNA by hybridization using either or both of the probes 5' TCAACAACAG TTTCTACAGA 3' (see SEQ ID NO:3) and 5' CCATTTTCCCTTGGTTTGCTC 3'.

Further objects and aspects of the present invention will be apparent from the description and examples that follow.

BRIEF DESCRIPTION OF THE FIGURES

FIG. 2A. Agarose Gel Electrophoresis and Differential Hybridization analysis of Amino Terminal VP1 Genome Fragments, illustrating the positive hybridization results obtained using the genotype III probe, -2328. The top portion illustrates the ethidium bromide stained agarose gel of PCR amplified products, while the bottom panel shows Southern blot hybridization results. Lane 1=GA76; Lane 2=India90; Lane 3=Nepal90; Lane 4=Montana90; Lane 5=AZ79; Lane 6=AK76; STD - Phi X Hae III standards (top to bottom) 1353, 1078, 876, 603, 310, 281 and 271, 235, 194, 118, and 72bp.

FIG. 2B. Agarose Gel Electrophoresis and Differential Hybridization analysis of Amino Terminal VP1 Genome Fragments, showing the hybridization analysis obtained using genotype I probe, +2232. The top portion illustrates the ethidium bromide stained agarose gel of PCR amplified products, while the bottom panel shows Southern blot hybridization results, containing identical PCR amplified fragments as FIG. 2A in the respective lanes. Lane 1=GA76; Lane 2=India90; Lane 3=Nepal90; Lane 4=Mantana90; Lane 5=AZ79; Lane 6=AK76; STD - Phi X Hae III standards (top to bottom) 1353, 1078, 876, 603, 310, 281 and 271, 235, 194, 118, and 72bp.

FIG. 3. Sequence Obtained from PCR Amplified Products for the First 171 VP1 Nucleotides (see SEQ ID NOS:6,7,8 and 9). The consensus sequence is shown on the top line and conserved residues are indicated by the dashes. Positions of nucleotide variability are indicated by the appropriate nucleotide.

FIG. 5. Sequence of probes used for differential detection of Genotype I (A) (see SEQ ID NO:3) and Genotype III (B) (see SEQ IN NO:4)

DETAILED DESCRIPTION OF THE INVENTION

Figure 1:
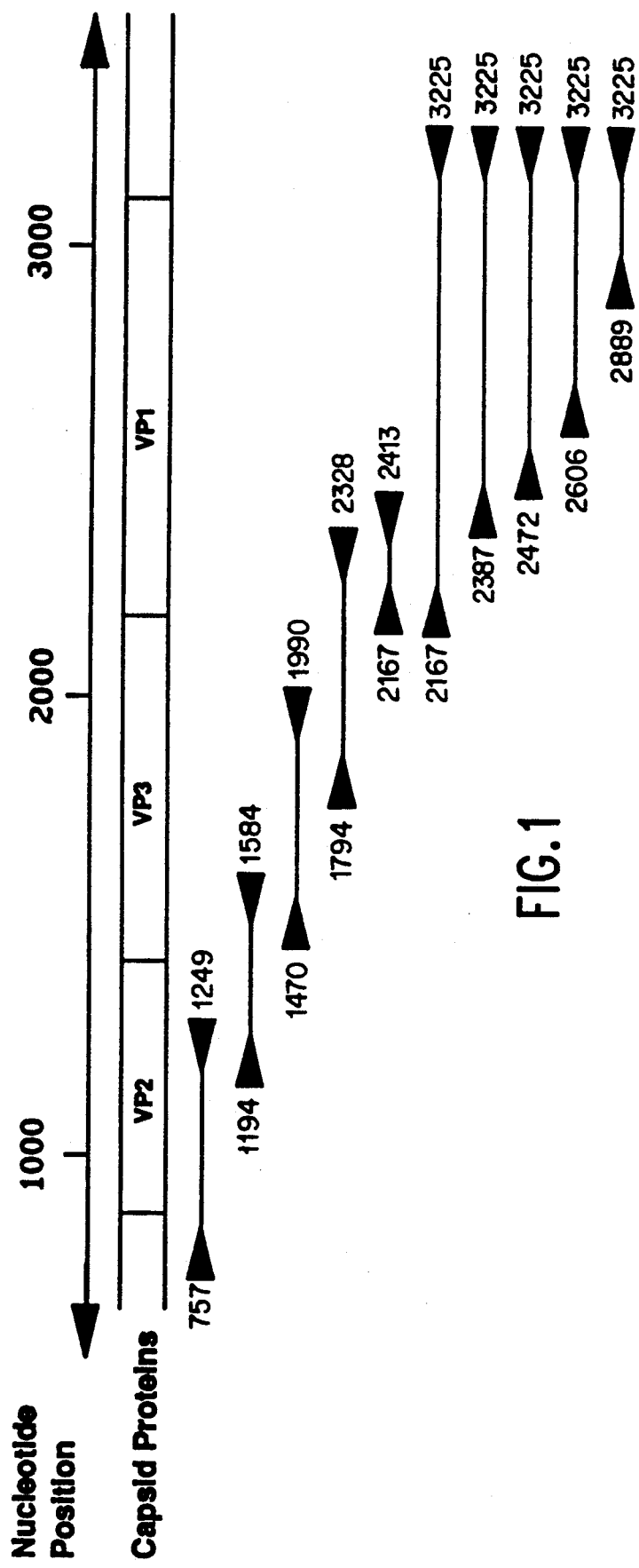
FIG. 1. Location of Primer Pairs Used for PCR Amplification of VP1, VP2 and VP3 Capsid Region of the GA76 HAV Isolate. The lines bordered by the inverse arrow heads indicate the length of the PCR product obtained using the appropriate positive and negative sense primers. Each number indicates the 5' end of the respective primer and corresponds to the extreme ends of the PCR product. (All nucleotide numbers represent the equivalent position within HM175 (Cohen et al., J. Vir. 61:50 (1987)). The corresponding genome and translated polypeptide region covered by these fragments are shown at the top of the Figure.
Figure 4:
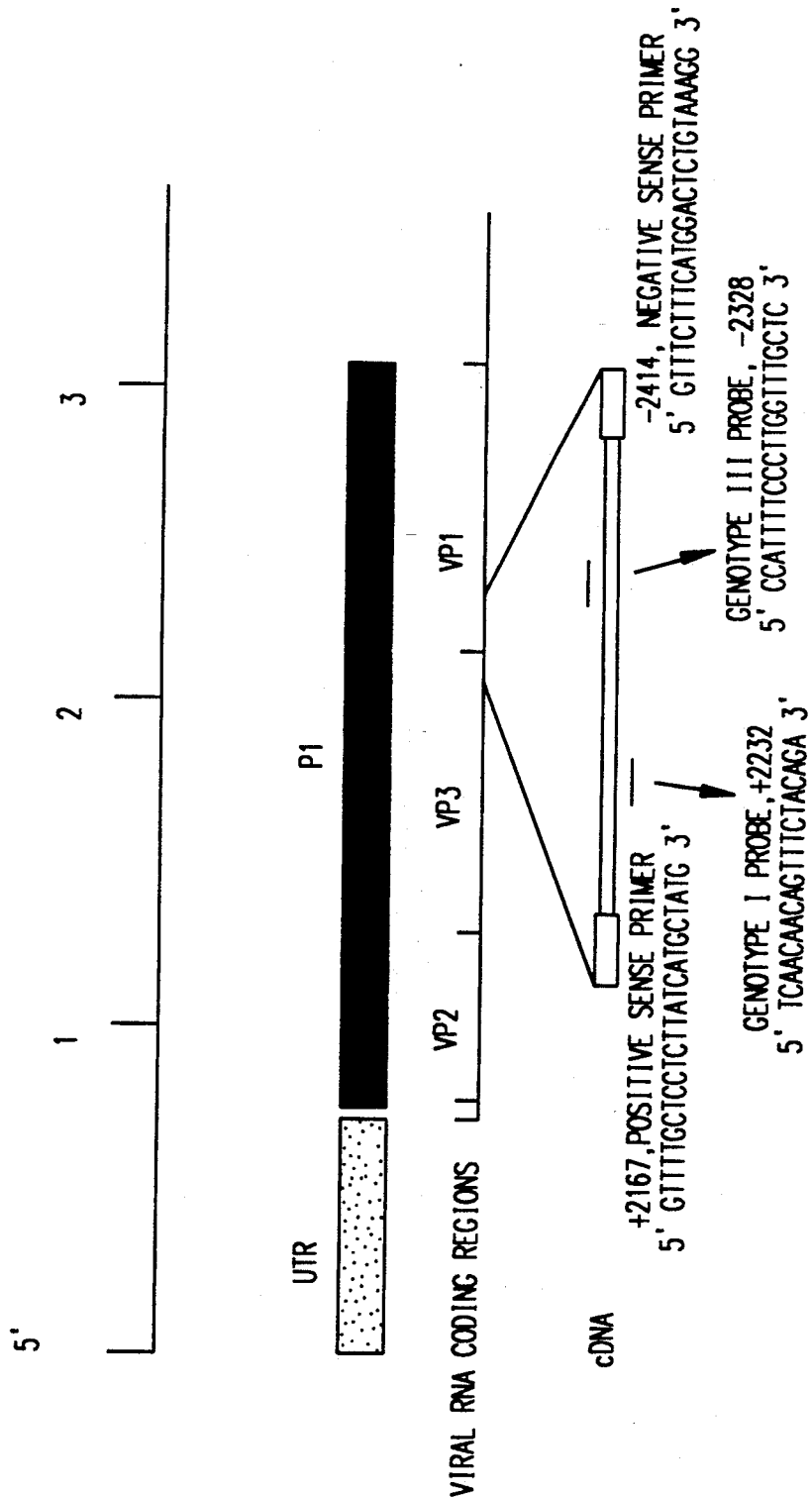
FIG. 4. Location of PCR primers and Probes (see SEQ ID NOS:1, 2, 3 and 4). This figure represents the region of the HAV sequence amplified regions showing the sequence of the primer binding sites (boxed area) and the location and sequence of the detecting probes (heavy lines) used for detection of amplified product.

There is currently no serological method for differentiating wild-type isolates of HAV. However, genetic analyses of PCR amplified products have afforded the means to differentiate various isolates based upon nucleic acid sequence. The information derived from these investigations has resulted in thedelineation of at least six genotypes of HAV (three human, and three simian-derived viruses). The genetic variant of HAV described herein was derived from a human case of clinical hepatitis A and subjected to a naive chimpanzee passage. The nucleic acid and translated amino acid sequence verify that it is related to PA21, a distinct genotype of HAV which was originally isolated from Panamanian owl monkeys (LeDuc et al., Lancet II:1427 (1981; Lemon et al., Infection and Immunity 42:418 (1982)). These two related isolates are genetically unique compared with other strains of HAV which have been sequenced to date (Baroudy et al., pNAS USA 82:2134 (1985); Linemeyer et al., J. Vir. 61:735 (1985); Najarian et al., pNAS USA 82:2627 (1985); Ovchinnikov et al., Dokl Akad. Nauk SSSR 285:1014 (1985); Paul et al., Virus Res. 8:153 (1987); Robertson et al., Virus Res. 8:309 (1987)). Accordingly, the present invention relates to a method of determining the presence of HAV using primers which have readily amplified all isolates examined thus far. The invention also relates to a method of selectively delineating two of the human genotypes, which appear to be the more common HAV isolates responsible for illness in different parts of the world.

Samples which contain free virus (for example, stool, environmental samples, or other fomite associated material) are selectively removed from adventitious material by immunoselection of whole virus using high titer anti-HAV antibodies coated onto a solid phase. The viral RNA is then, denatured in the presence of a specific primer (5' GGAAATGCTCAGGTACTTTCTTG 3' (see SEQ ID NO:1), referred hereinafter as -2414) one of which is designed to bind to the virus RNA in a negative sense, and the viral RNA is reverse transcribed to cDNA using standard methodology.

At this stage, two approaches for dectection of amplified cDNA can be used. For rapid diagnosis of HAV positive containing material, the second primer (5' GTTTTGCTCCTCTTTATCATGCTATG 3', (see SEQ ID NO:2), referred hereinafter as +2167), which is virus sense is labeled at the 5' end with, for instance, radioactivity or a chromogenic substrate, and added to the above-described cDNA just prior to amplification by polymerase chain reaction (PCR). The viral cDNA is then amplified by the PCR using, for example, Taq polymerase. The resulting product, labeled at the 5' end, can be separated by, for instance, agarose or acrylamide gel electrophoresis, and the labeled band can be detected using standard methods, such as by exposure of the radioactivity or by color development.

Alternatively, the PCR can be performed with unlabeled primers, -2414 and +2167, and can be subjected to for example, agarose electrophoresis. The agarose gel can be transferred to nitrocellulose and hybridized, using standard techniques, with a probe which selectively binds to the respective genotype of HAV. For instance, a probe that will selectively bind with genotype I is 5' TCAACAACAG TTTCTACAGA 3' (see SEQ ID NO:3). Likewise, a probe that will selectively bind with genotype III is 5' CCATTTTCCCTTGGTTTGCTC 3' (see SEQ ID NO:4). An example of the differential hybridization using these probes is shown in FIG. 2.

In one embodiment, the present invention relates to a method for detecting the presence of HAV in a sample, which entails capturing whole HAV virus by using antibodies specific to HAV and isolating viral RNA using standard methodology. The viral RNA is then denatured in the presence of a primer designed to bind to the viral RNA in a negative sense (-2414, 5' GGAAATGTCTCAGGTACTTTCTTTG 3'(see SEQ ID NO:). After annealing with that primer, a cDNA copy of the RNA is generated by reverse transcription. A second primer (+2167, 5' GTTTTGCTCCTCTTTATCATGCTATG 3' (see SEQ ID NO:2)), is then added, which is virus sense and labeled at the 5' end. That second primer anneals to the cDNA. Then the annealed cDNA is amplified by polymerase chain reaction, using standard methods, and the amplified cDNA is detected.

In a second embodiment, the present invention relates to a method for detecting genotypes I or III of HAV. First, whole HAV virus is captured using antibodies specific to HAV and viral RNA is isolated. The viral RNA is isolated using standard methodology and positive and negative sense primers designed to bind to the viral nucleic acid. After the RNA anneals with the negative sense primer (-2414), a cDNA copy of the RNA is generated by reverse transcription. The cDNA is then amplified by polymerase chain reaction using both the positive sense primer (+2167) and the negative sense primer described above, and the amplified cDNA is detected as HAV DNA by hybridization using either or both of the probes 5' TCAACAACAGTTTCTACAGA 3' (see SEQ ID NO:3) and 5' CCATTTTCCCTTGGTTTGCTC 3' (see SEQ ID NO:4).

In another embodiment, the present invention relates to a method for detecting genotype I of HAV. This is accomplished by capturing whole HAV virus by using antibodies specific to HAV and isolating viral RNA. The viral RNA is then denatured in the presence of primers designed to bind to viral genome sequences (+2167 and -2414). After annealing the viral RNA with the negative sense primer, a cDNA copy of the RNA is generated by reverse transcription. The cDNA is amplified by polymerase chain reaction using both the negative sense and positive sense primers, and the amplified cDNA is detected as HAV DNA by standard hybridization techniques using the probe 5' TCAACAACAG TTTCTACAGA 3 (see SEQ ID NO:3). In a further embodiment of the present invention, a method for detecting genotype III of HAV is accomplished by following the same steps described for detecting genotype I, where the probe used in hybridization is 5' CCATTTTCCCTTGGTTTGCTC 3' (see SEQ ID NO:4).

The invention is further described by the following non-limiting examples.

EXAMPLES

The following technical protocols are used in the examples that follow.

Virus Sources. Human HAV isolates were stool specimens stored at —70° C. The GA76 isolate was from an individual infected during a community outbreak in Georgia, USA in 1976. Virus containing stool specimens collected 13, 11, 9 and 7 days prior to the onset of symptoms (—13 to —7 days) were available. The India 90 isolate was from a child infected during an outbreak in a childcare facility in northern India in 1990. Stool was collected approximately 7 days after the onset of symptoms. The Nepal 89 and Nepal 90 isolates (cases TK-023/89 and TK-017/90) were from a young adult and child, respectively, infected during 1989 and 1990 in the Kathmandu Valley of Nepal. Stools were collected 4 and 6 days after the onset of symptoms, respectively.

Animal Infectivity. One ml of the 10%, minus 11 day GA76 human stool supernatant was inoculated intravenously into an experimentally naive chimpanzee (Austin, #1394). Serial stool samples were collected and analyzed by polymerase chain reaction (PCR) as described below and enzyme-linked immunoabsorbant assay (EIA) (Wheeler et al., J. Vir. 58:307 (1987)) for viral excretion. Biweekly serum samples were tested colorimetrically for alanine aminotransferase (ALT) liver enzyme labels and anti HAV antibodies using the HAVAB assay (Abbott Laboratories, North Chicago).

Primers and Probes Used for PCR Amplification and Southern Blot Hybridization. A set of positive and negative sense synthetic oligonucleotide primers, +2167 and -2414 (Robertson et al., J. Infectious Dis. 163:286 (1991)) Were used to amplify the amino terminal portion of the VPI coding region for genotype, evaluation and viral excretion. The genotype III probe (hereinafter referred to as —2328), based upon a common sequence between GA76 and PA21, was identified in the VPI amino terminus coding region (nucleotides. 2328-2308, 5' CCATTTTCCCTTGGTTGCTC 3' (see SEQ ID NO:4)) and used for identification of this genotype by Southern blot hybridization. The genotype I synthetic oligonucleotide probe, (probe +2232, nucleotides 2232-2251, 5' TCAACAACAGTTTCTACAGA 3' (see SEQ ID NO:3) was designed to recognize a conserved sequence selected by comparison of published HAV sequences (Robertson et al., J. Infectious Dis. 163:286 (1991)).

The probes described above were kinase-labeled and used for hybridization analysis. After hybridization with probe —2328, membranes were washed once at room temperature and once at 37° C. for 20 minutes each, using 2X SSC-0.01% SDS. Membranes hybridized with probe +2232 were washed twice at room temperature for 20 minutes using 2X SSC-0.01%.

Multiple primer pairs used for amplification of the VP1, VP2 and VP3 coding region of the GA76 capsid are schematically illustrated in FIG. 1. Initial amplification of the entire VP1 coding region was performed using two primers. The negative sense primer, nucleotides 3208-3225 (5' CATTTTCCTAGGAGGTGG 3' (see SEQ ID NO:5)) was complementary to a segment of the 5' end of the P2 genome; the positive sense primer, located in the carboxy terminal region of the VP3, was the same positive sense oligonucleotide primer (+2167) described previously. These primers resulted in a product which was approximately one half the expected length. Subsequent amplification of the remaining portion of the VP1 gene was accomplished using specific primers designed based upon sequence obtained from the previous amplified product. The primer pairs chosen for amplification of the VP2 and VP3 genes were based upon common conserved sequences between PA21 and HM-175.

Amplification, cDNA Purification and Nucleic Acid Sequencing of GA76 P1 Genome Region. The RNA derived from antibody captured virus was converted to cDNA with reverse transcriptase (Boehringer Mannheim, Indianapolis, Ind.) and the resulting ss cDNA amplified by the polymerase chain reaction (RT-PCR) (Saiki et al., Science 230:1350 (1985); Scharf et al., Science 233:1076 (1986)) as described previously (Robertson et al., Virus Res. 13:207 (1989); Robertson et al.,, J. Infectious Dis. 163:286 (1991)) with the exception of the annealing temperature which was adjusted from 55° C. to 45° C. The PCR amplified products were purified by polyacrylamide gel electrophoresis (Brown and Robertson, Biotechniques 8:10 (1990)) and sequenced by dideoxynucleotide termination reactions (Sanger et al., PNAS USA 74:5463 (1977); Tabor & Richardson, pNAS USA 84:4767 (1987); Winship, Nucleic Acids Res. 17:1266 (1989)) as previously described by Robertson et al. (1991) using the appropriate positive and negative sense primers used for PCR amplification. Computer algorithms designed for the Vax computer and provided by the University of Wisconsin (Devereux et al; Nucleic Acids Res. 12:387 (1983)) were used for sequence analysis and alignment.

EXAMPLE 1

Infectivity of GA76 HAV Isolate. Nucleic acid sequencing of the amino terminal region of GA76 VP1 gene (Robertson et al., J. Infectious Dis. 163:286 (1991)) indicated that this isolate was genetically related to PA21, and therefore differed significantly from other known human HAV isolates. A chimpanzee was infected with the GA76 isolate to provide sufficient quantity of virus for detailed genetic analysis and to verify whether the genetic differences of this genotype resulted in an altered phenotypic expression of illness. The animal developed classical symptoms of hepatitis A with liver enzyme elevations occurring within two weeks of inoculation, and seroconversion to anti-HAV positive status. Viral antigen was detected by EIA in stools from day 8 post inoculation until the peak of liver enzyme elevation, while evaluation of viral nucleic acid by RT-PCR amplification and hybridization with genotype III probe (−2328, 5' CCATTTTCCCTTGGTTTGCTC 3' (see SEQ ID NO:4)) revealed that excretion began approximately 3 days after infection and continued for a week after the return of liver enzymes to normal. As was found in the majority of Panamanian owl monkeys challenged with genotype I virus (HM-175; Brown EA, et al., J. Vir. 63:4932 (1989); challenge of this animal with genotype I virus (AK76; Robertson et al., J. Infectious Dis. 163:286 (1991)) resulted in no liver enzyme elevation and no detectible virus replication buy either EIA or RT-PCR amplification and hybridization. The data indicates that the two genotypes induce cross protective antibodies.

EXAMPLE 2

Nucleic and Amino Acid Sequence of GA76 PI Genome Region. Since preliminary evidence indicated that the GA76 HAV isolate was genetically related to Panamanian owl monkey derived HAV (PA21) and differed significantly from other HAV isolates classified as genotype I, a more detailed analysis of the exposed capsid polypeptides was completed. Nucleic acid sequencing of the GA76 VP1, VP2, and VP3 coding regions confirmed that 97% of the nucleotides were conserved when compared with PA21 (Brown, E. A. et al., J. Vir. 63:4932 (1989)). The nucleotide positions which differ between these two isolates are shown in Table I and reveal that the majority of the nucleotide changes within these polypeptides are within the VP1 genome region. Although the nucleotide sequences of PA21 and GA76 are similar, they differ approximately 20% from published sequences of human-derived HAV isolates (Baroudy et al., PNAS USA 82:2134 (1985); Linemeyer et al., J. Vir. 54:247 (1985); Najarian et al., PNAS USA 82:2627 (1985); Ovchinnikov et al., Dokl. Akad. Nauk. SSSR 285:1014 (1985); Paul et al., Virus Res. 8:153 (1987); Robertson et al., Virus Res. 8:309 (1987)).

TABLE I

| Nucleotide Differences Between PA21 and GA76 | | | | | | | | |
|---|---|---|---|---|---|---|---|---|
| VP2 | PA21 | GA76 | VP3 | PA21 | GA76 | VP1 | PA21 | GA76 |
| 893* | T | C | 1565 | T | C | 2213 | G | A |
| 938 | C | T | 1643 | T | C | 2234 | T | C |
| 990 | G | A | 1700 | G | A | 2770 | T | C |
| 1004 | C | T | 1731 | C | T | 2279 | C | T |
| 1238 | T | C | 1793 | C | T | 2282 | T | C |
| 1262 | C | T | 1914 | T | C | 2291 | G | T |
| 1270 | T | C | 1934 | C | G | 2331 | G | A |
| 1298 | T | C | 1961 | A | T | 2340 | A | G |
| 1394 | T | C | 1976 | A | G | 2354 | A | G |
| | | | 1982 | T | C | 2362 | C | T |
| | | | 2027 | T | C | 2375 | G | A |
| | | | 2135 | T | C | 2399 | G | A |
| | | | 2141 | T | C | 2411 | C | T |
| | | | | | | 2465 | C | T |
| | | | | | | 2478 | C | T |
| | | | | | | 2492 | A | G |
| | | | | | | 2495 | T | C |
| | | | | | | 2537 | T | C |
| | | | | | | 2540 | C | T |
| | | | | | | 2597 | T | C |
| | | | | | | 2697 | T | C |
| | | | | | | 2699 | A | G |
| | | | | | | 2708 | T | C |

TABLE I-continued

| | Nucleotide Differences Between PA21 and GA76 | | | | | | | |
|---|---|---|---|---|---|---|---|---|
| VP2 | PA21 | GA76 | VP3 | PA21 | GA76 | VP1 | PA21 | GA76 |
| | | | | | | 2741 | T | C |
| | | | | | | 2783 | T | C |
| | | | | | | 2840 | C | T |
| | | | | | | 2867 | C | T |
| | | | | | | 2888 | A | G |
| | | | | | | 2912 | T | C |
| | | | | | | 2918 | T | C |
| | | | | | | 2951 | C | T |
| | | | | | | 3030 | A | G |

*Nucleotide numbers represent the equivalent position within HM175 (Cohen et al., 1987)

Despite the extensive nucleic acid sequence divergence between the GA76 group and other human isolates of HAV, there were limited amino acid changes within the exposed capsid polypeptides which are shown in Table II. There are twenty amino acid changes which appear to be unique to the PA21/GA76 group. However, there are only four amino acid differences between PA21 and GA76 (VP2-63, V and I, VP1-42, V and I, VP1-45, V and I, VP1-275, V and M) which are all homologous amino acid changes. These data provide conclusive evidence that the GA76 strain of HAV is genotype III and that this genotype causes human illness.

EXAMPLE 3

Evidence for Other HAV Outbreaks Caused by GA76/PA21-like Genotype. Thus far, this unique genotype has been implicated in only two outbreaks of HAV, one in Sweden in 1979 (H-122, Jansen et al., PNAS USA 87:2867 (1990)), and the outbreak which yielded the GA76 isolate (Robertson et al., J. Infectious Dis. 163:286 (1991)). During our attempts to characterize genetically distinct isolates of HAV from different geographic locations, stool samples were obtained from cases of hepatitis in a child care facility in northern India, during the summer of 1990 (India 90). In addition, stool samples (TK 023/89, TK 017/90) derived from the Kathmandu Valley in Nepal during the summer months of 1989 and 1990, were also evaluated to determine the genotype of virus causing infection.

Hybridization probes which were designed to differentiate between genotypes were used to evaluate the amplified products of HAV obtained from different outbreaks. FIG. 2 illustrates two ethidium bromide stained agarose gels with identical samples from amplification of the amino terminal region of the VP1 genome.

TABLE II

| | Amino Acid Differences Within Exposed Capsid Polypeptides | | | | | | |
|---|---|---|---|---|---|---|---|
| | HM175 | MBB | LA | HAS-15 | CR326 | PA21 | GA76 |
| VP2-2[a] | I | — | — | — | — | V | V |
| VP2-12 | D | — | — | — | V | — | — |
| VP2-37 | S | — | — | — | L | — | — |
| VP2-40 | V | — | I | I | I | P | P |
| VP2-51 | G | — | — | — | S | — | — |
| VP2-54 | K | — | — | — | — | R | R |
| VP2-63 | I | — | — | — | — | V | — |
| VP2-131 | G | — | — | — | S | — | — |
| VP2-189 | E | — | — | — | D | — | — |
| VP3-39 | P | — | — | — | — | A | A |
| VP3-93 | D | — | — | — | — | E | E |
| VP3-144 | S | — | T | T | T | — | — |
| VP3-145 | G | — | — | — | — | H | H |
| VP3-189 | A | — | — | — | — | S | S |
| VP3-200 | K | — | — | — | N | — | — |
| VP1-15 | E | — | — | — | — | K | K |
| VP1-28 | M | — | — | * | — | V | V |
| VP1-34 | K | — | — | — | — | R | R |
| VP1-37 | R | — | — | — | — | Q | Q |
| VP1-42 | V | — | — | — | — | — | I |
| VP1-45 | V | — | — | — | — | I | — |
| VP1-59 | V | — | — | — | A | — | — |
| VP1-174 | E | — | — | K | — | — | — |
| VP1-189 | R | — | — | — | T | — | — |
| VP1-247 | C | — | — | — | S | — | — |
| VP1-253 | E | — | — | — | Q | — | — |
| VP1-266 | S | — | — | — | — | T | T |
| VP1-270 | L | — | — | — | — | M | M |
| VP1-272 | T | — | — | — | — | S | S |
| VP1-274 | S | — | — | — | — | T | T |
| VP1-275 | M | — | — | — | — | — | V |
| VP1-277 | S | — | — | — | — | D | D |
| VP1-281 | A | — | — | — | — | L | L |
| VP1-293 | S | — | — | — | — | T | T |
| VP1-297 | K | — | R | R | R | R | R |

TABLE II-continued

| | Amino Acid Differences Within Exposed Capsid Polypeptides | | | | | | |
|---|---|---|---|---|---|---|---|
| | HM175 | MBB | LA | HAS-15 | CR326 | PA21 | GA76 |
| VP1-298 | R | — | — | — | — | K | K |

*The position of the variable amino acids is designated by the capsid polypeptide followed by the amino acid position within the individual protein. The dashes represent identity with HM-175 amino acid, while changed amino acids are shown by the respective single letter code. The star indicates a deletion within the HAS-15 VP1 amino terminal region.

Lanes 1, 2, and 3 contain PCR products from GA76, India 90 and Nepal 90, respectively; lanes 4, 5, and 6 contain North American isolates previously characterized to be members of the HAV genotype I (Robertson et al., J. Infectious Dis. 163:286 (1991)). As shown in the bottom panels, the genotype III probe bound specifically to the India 90, Nepal 90, and GA76 products with no detectable binding to the North American isolates. In contrast, the genotype I probe derived from a conserved region of published sequences (Baroudy et al., PNAS USA 82:2134 (1985); Linemeyer et al., J. Vir. 54:247 (1985); Najarian et al., PNAS USA 82:2627 (1985; Ovchinnikov et al., 1985); Paul et al., Virus Res. 8:153 (1987); Robertson et al., Virus Res. 8:309 (1987)) bound preferentially to the isolates from North America with limited cross-reactivity to the Nepal sample.

The relatedness of three separate isolates from Nepal and India to the GA76 and PA21 viruses was verified by nucleic acid sequencing of the amplified products. The results, shown in FIG. 3, illustrates the genetic relatedness of these isolates (India and Nepal) to GA76 and PA2I, and the differences when compared with HM-175, a prototype of the more common HAV genotype. Genetic analysis revealed that 94–97% of the nucleotides were conserved compared to each other and the GA76 or PA21 HAV sequence in this region. The translated amino acid sequence of these isolates revealed that only positions VP1-42 and VP1-45 varied when compared to each other, PA21, or GA76. The India and Nepal isolates contained an isoleucine at position VP1-42, while the Nepal 90 isolate contained an isoleucine substitution at position VP1-45.

The entire contents of all references cited herein above are incorporated by reference.

While the foregoing invention has been described in some detail for purposed of clarity and understanding, it will be clear to one skilled in the art from a reading of this disclosure that various changes in form and detail can be made without departing from the true scope of the invention.

What is claimed is:

1. A method for detecting hepatitis A virus comprising the steps of:
    (i) capturing whole hepatitis A virus with antibodies specific to hepatitis A virus;
    (ii) generating a cDNA copy of the viral RNA by reverse transcription in the presence of a negative strand primer consisting of the nucleotides defined by SEQ ID NO:1;
    (iii) amplifying the cDNA of step (ii) by polymerase chain reaction with both said negative strand primer and a positive strand primer consisting of the nucleotides defined by SEQ ID NO: 2, said positive strand primer being labeled at the 5' end and wherein the amplification product can be used to distinguish hepatitis A genotypes I and III; and
    (iv) detecting the amplified cDNA of step (iii), wherein the presence of detectable amplification indicates the presence of hepatitis A virus.

2. A method for detecting Genotype I of hepatitis A virus comprising the steps of:
    (i) capturing whole hepatitis A virus with antibodies specific to hepatitis A virus;
    (ii) generating a cDNA copy of the viral RNA by reverse transcription in the presence of a negative strand primer consisting of the nucleotides defined by SE ID NO:1;
    (iii) amplifying the cDNA of step (ii) by polymerase chain reaction with both said negative strand primer and a positive strand primer consisting of the nucleotides defined by SEQ ID NO: 2; and
    (iv) detecting the amplified cDNA of step (iii) by hybridization with the probe consisting of the nucleotides defined by SEQ ID NO:3, wherein the presence of detectable hybridization indicates the presence of Genotype I of hepatitis A virus.

3. A method for detecting Genotype III of hepatitis A virus comprising the steps of:
    (i) capturing whole hepatitis A virus with antibodies specific to hepatitis A virus;
    (ii) generating a cDNA copy of the viral RNA by reverse transcription in the presence of a negative strand primer consisting of the nucleotides defined by SEQ ID NO:1;
    (iii) amplifying the cDNA of step (ii) by polymerase chain reaction with both said negative strand primer and a positive strand primer consisting of the nucleotides defined by SEQ ID NO:2; and
    (iv) detecting the amplified cDNA of step (iii) by hybridization with the probe consisting of the nucleotides defined by SEQ ID NO:4, wherein the presence of detectable hybridization indicates the presence of Genotype III of hepatitis A virus.

4. A DNA primer that hybridizes with hepatitis A virus, consisting of the sequence defined by SEQ ID NO:1.

5. DNA primer that hybridizes with hepatitis A virus, consisting of the sequence defined by SEQ ID NO: 2.

6. A DNA probe that hybridizes with hepatitis A virus genotype I, consisting of the sequence defined by SEQ ID NO:3.

7. A DNA probe that hybridizes with hepatitis A virus genotype III, consisting of the sequence defined by SEQ ID NO:4.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GTTTCTTTCA TGGACTCTGT AAAGG        25

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GTTTTGCTCC TCTTATCATG CTATG        25

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TCAACAACAG TTTCTACAGA　　　　　　　　　　　　　　　　　　　　　　　　20

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CCATTTCCC TTGGTTTGCT C　　　　　　　　　　　　　　　　　　　　　　　　21

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CATTTCCTA GGAGGTGG　　　　　　　　　　　　　　　　　　　　　　　　　　18

( 2 ) INFORMATION FOR SEQ ID NO:6:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GTTGGAGATG ATTCTGGAGG CTTCTCTACC ACTGTTTCAA CAAAACAGAA　　　　　50

( 2 ) INFORMATION FOR SEQ ID NO:7:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

TGTTCCAGAC CCCCAAGTTG GTATCACAAC AGTGAAGGAT CTTAAAGGTA　　　　　50

( 2 ) INFORMATION FOR SEQ ID NO:8:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GAGCAAACCA AGGGAAAATG GATATTTCGG GTGTCCAAGC TCCTGTGGGA　　　　　50

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GCTATTACTA CCATTGAAGA T                21